United States Patent [19]
Lin et al.

[11] Patent Number: 5,557,029
[45] Date of Patent: Sep. 17, 1996

[54] ISOMERIZATION OF SATURATED HYDROCARBONS

[75] Inventors: Fan-Nan Lin; Nak J. Sung, both of Bartlesville, Okla.; Stephen L. Ege; Thomas A. Lessard, both of Borger, Tex.

[73] Assignee: Phillips Petroleum Company, Bartlesville, Okla.

[21] Appl. No.: 523,978

[22] Filed: Sep. 6, 1995

[51] Int. Cl.$^6$ .................................................. C07C 5/13
[52] U.S. Cl. ...................... 585/739; 585/734; 585/743; 585/744; 585/750; 585/751
[58] Field of Search ........................... 585/734, 739, 585/743, 744, 750, 751

[56] References Cited

U.S. PATENT DOCUMENTS

| | | | |
|---|---|---|---|
| 3,248,320 | 4/1966 | White et al. | 208/136 |
| 3,558,734 | 1/1971 | Myers. | |
| 3,658,689 | 4/1972 | Steinmetz et al. | 208/46 |
| 3,723,556 | 3/1973 | Wilhelm | 585/751 |
| 4,778,944 | 10/1988 | Zarchy | 585/739 |
| 4,827,076 | 5/1989 | Kokayett et al. | 585/739 |
| 4,835,129 | 5/1989 | Travers et al. | 502/37 |
| 4,937,215 | 6/1990 | Murakawa et al. | 502/36 |
| 5,003,118 | 3/1991 | Low et al. | 585/253 |
| 5,336,834 | 8/1994 | Zarchy et al. | 585/750 |

*Primary Examiner*—Anthony McFarlane
*Assistant Examiner*—E. D. Irzinski
*Attorney, Agent, or Firm*—K. K. Brandes

[57] ABSTRACT

In a process for isomerizing saturated $C_4$–$C_{10}$ hydrocarbons (preferably n-pentane) in the presence of a platinum/zeolite catalyst, wherein sulfur compounds are present in the feed as impurities and cause catalyst deactivating, at least one volatile chlorine compound (preferably tetrachloroethylene or carbon tetrachloride) is added to the feed in an amount sufficient to counteract the catalyst deactivation. A correlation between effective amounts of chloride additive(s) required to counteract the catalyst deactivating effect caused by specific sulfur compound(s) and a specific parameter of various sulfur compounds has been established. The water content in the isomerization feed is not to exceed about 60 ppm $H_2O$ (based on the weight of the at least one feed hydrocarbons.

37 Claims, 1 Drawing Sheet

ISOMERIZATION OF SATURATED HYDROCARBONS

BACKGROUND OF THE INVENTION

The present invention relates to a process for alkane and/or cycloalkane isomerization in the presence of feed impurities.

The use of supported platinum catalysts (such as platinum on a zeolite) for isomerizing saturated hydrocarbons, in particular normal alkanes to isoalkanes (such as n-pentane to isopentane), is well known. Impurities, in particular sulfur compounds, which are present in the feed can cause a rapid decrease in catalyst activity. Pretreatment of the feed prior to the isomerization to remove a major portion of these impurities is one option to alleviate or eliminate this catalyst deactivation, but this route is expensive because additional equipment and operating costs are required. Also, the levels of these impurities in the feed may fluctuate, and pretreatment of the feed may not always be adequate. Another option to alleviate the deactivation of isomerization catalysts by sulfur impurities is to operate the isomerization processes at relatively high hydrogen to hydrocarbon ratios and at relatively high temperatures. However, this route is also expensive and generally produces undesirably high amounts of by-products, mainly light gases which are formed by hydrocracking of feed hydrocarbons. The present invention is directed to a more effective method of alleviating, and even eliminating, catalyst deactivation problems caused by the presence of sulfur impurities in isomerization feeds which comprises injecting an additive into the feed to counteract detrimental effects caused by these impurities. The amount of the injected additive is generally correlated with the types and levels of sulfur compounds which are present as impurities in the feed so as to alleviate, or even completely eliminate, catalyst deactivating effects caused by these sulfur compounds.

SUMMARY OF THE INVENTION

It is an object of this invention to carry out the isomerization of a feed comprising alkane(s) and/or cycloalkane(s), hydrogen gas and also sulfur impurities in the presence of a zeolite-supported platinum catalyst and in the presence of feed additive(s) so as to alleviate, or essentially eliminate, the deactivation of the catalyst by these sulfur impurities. Other objects and advantages will become apparent from the detailed description and the appended claims.

According to this invention, in an isomerization process for converting at least one saturated feed hydrocarbon selected from the group consisting of alkanes (preferably normal, linear alkanes) containing 4–10 carbon atoms per molecule and cycloalkanes containing 5–10 carbon atoms per molecule to at least one saturated product hydrocarbon isomer, wherein a feed stream which comprises (i) said at least one saturated feed hydrocarbon, (ii) hydrogen gas, (iii) about 0 to about 60 ppm water (based on the weight of said at least feed hydrocarbon, i.e., 0–60 parts by weight of water as an impurity per million parts by weight of said at least one saturated feed hydrocarbon), and (iv) at least one sulfur compound (as impurity) is contacted in a reaction zone at effective isomerization conditions with a catalyst which comprises platinum and at least one zeolite but which is essentially free of halides, wherein deactivation of said catalyst by said at least one sulfur compound occurs in said reaction zone, the improvement comprises the presence of at least one added chlorine compound selected from the group consisting of hydrogen chloride and organic chlorides in said reaction zone in an amount sufficient to essentially eliminate the deactivation of said catalyst caused by said at least one sulfur compound and to maintain a substantially constant conversion of said at least one saturated feed hydrocarbon to said at least one saturated product hydrocarbon isomer at said effective isomerization conditions.

Preferably, the saturated feed hydrocarbon is n-pentane, which is isomerized in the process of this invention to isopentanes (2-methylbutane, 2,2-dimethylpropane or mixtures thereof). In a particular embodiment, the at least sulfur compound which is present as impurity in the isomerization feed stream is selected from the group consisting of hydrogen sulfide, carbon disulfide, carbonyl sulfide (COS), mercaptans, organic sulfides, organic disulfides and organic polysulfides. In another particular embodiment, the feed comprising said at least one saturated feed hydrocarbon is analyzed so as to determine the concentration of sulfur attributed to each specific sulfur compound (particularly each specific mercaptan, each specific organic sulfide, each specific organic disulfide and each specific organic polysulfide) being present in the feed, followed by calculating the amount of said at least one chlorine compound which must be added to the feed so as to counteract catalyst deactivation caused by the at least one sulfur compound and to maintain a substantially constant conversion of the saturated feed hydrocarbon to product isomer(s) at effective isomerization conditions. In a preferred embodiment, the injected chlorine compound is an organic chloride additive, more preferably tetrachloroethylene (also called perchloroethylene, PCE).

DETAILED DESCRIPTION OF THE INVENTION

Figure 1:
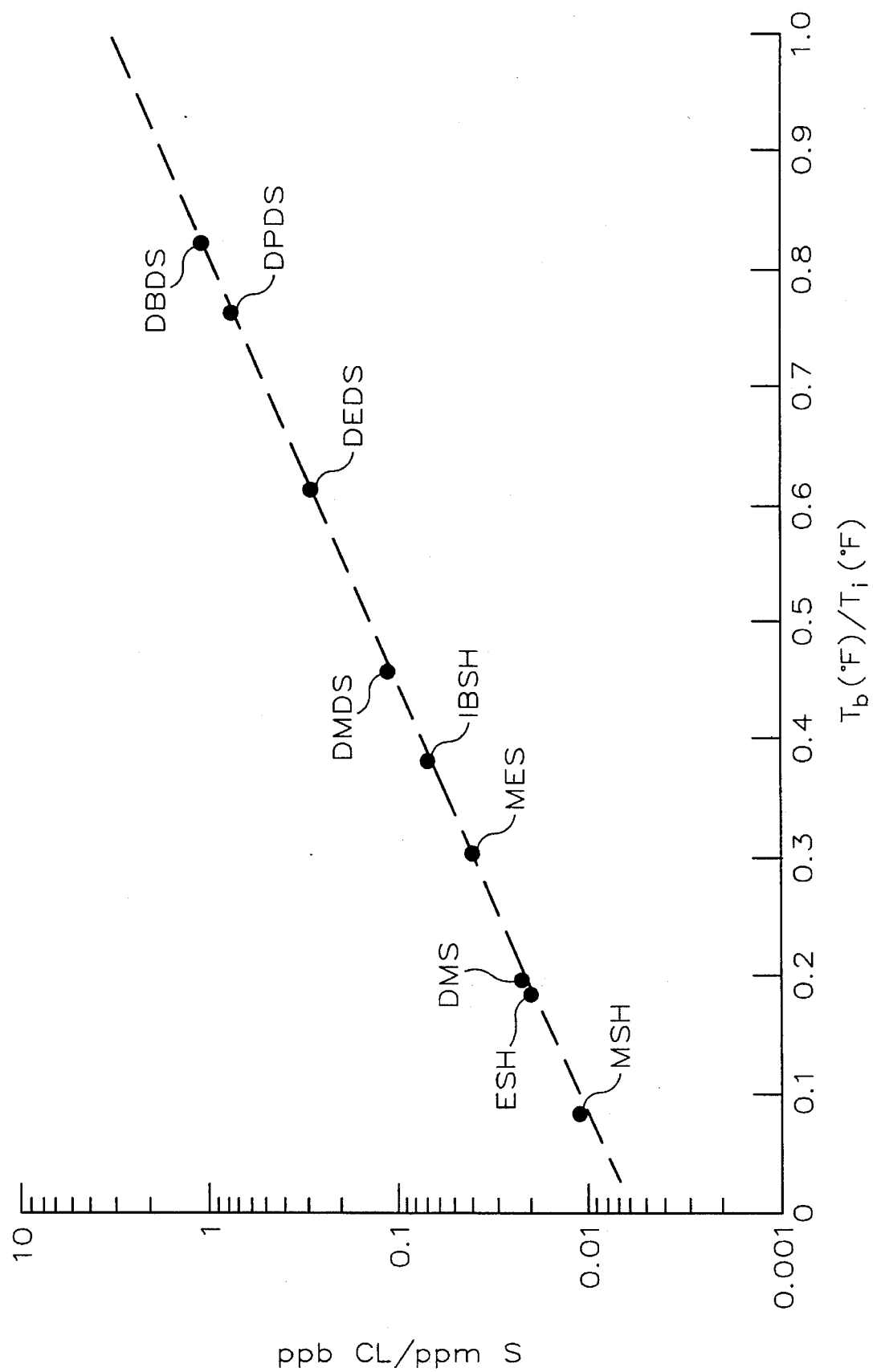
FIG. 1 illustrates the correlation between (a) the amount of added chloride (ppb Cl) required to eliminate the catalyst deactivating effect caused by 1 ppm S attributed to various sulfur compounds present in a n-pentane containing isomerization feed (which also contains up to about 30 ppm $H_2O$) and (b) the ratio of the normal boiling temperature ($T_b$, given in °F.) of each sulfur compound to the alkane isomerization temperature ($T_i$, in °F.).

Any straight-chain or branched alkane containing 4–10 C atoms per molecule can be employed as feed hydrocarbon in the isomerization process of this invention. Non-limiting examples of suitable alkanes include (but are not limited to) n-butane, n-pentane (presently preferred), n-hexane, 2-methylpentane, 3-methylpentane, n-heptane, 2-methylhexane, 3-methylhexane, octanes, nonanes, decanes, and mixtures thereof. Any cycloalkane containing 5–10 can also be used as feed hydrocarbon in the process of this invention. Non-limiting examples of suitable cycloalkanes include (but are not limited to) cyclopentane, cyclohexane, methylcyclopentane, cycloheptane, methylcyclohexane, cyclooctane, methylcyclooctane, and mixtures thereof. Mixtures of alkanes and cycloalkanes (in any proportion, such as from about 1 to about 99 weight-% of each) can also be employed as feed hydrocarbons.

Any effective catalyst which comprises platinum and one (or more than one) zeolite as the support material can be employed as the isomerization catalyst of this invention. Chemically bound halogens (i.e., fluoride or chloride or bromide or iodide) are substantially absent from the catalyst (i.e., no amounts above insignificant trace amounts of these halogens are present). Any effective zeolite can be employed as the support material. Non-limiting examples include (but are not limited to) zeolite X, zeolite Y, zeolite L, zeolite Beta, zeolite ZSM-5, zeolite ZSM-11, zeolite ZSM-12, zeolite ZSM-22, zeolite ZSM-23, zeolite ZSM-35, zeolite ZSM-48, erionite, mordenite (presently preferred), and the like, and mixtures thereof. Some of these Pt/zeolite catalysts are commercially available, e.g., from UOP, Des Plains, Ill. Generally, the platinum content in the catalyst ranges from about 0.05–2.0 (preferably about 0.1–1.0) weight-% Pt, and the surface area of the catalyst is about 100–800 $m^2/g$ (measured by the BET method). The catalyst can be fresh (unused) or it can be used and thereafter regenerated.

Any suitable isomerization (also referred to as hydroisomerization) conditions can be employed in the process of this invention. Generally, the saturated feed hydrocarbon(s) and hydrogen gas are premixed and are contacted with the catalyst (generally present in a fixed bed), at a reaction temperature of at least about 200° F., preferably at a temperature of about 200°–600° F. In the preferred case of n-pentane isomerization in the presence of $H_2$ gas, the average reaction temperature in the catalyst bed is about 450° F. to about 550° F. The molar ratio of hydrogen gas to saturated feed hydrocarbon(s) used in the alkane hydroisomerization process generally is within the range of about 0.01:1 to about 10:1, preferably about 0.1:1 to about 1:1. Generally, the liquid hourly space velocity of the hydrocarbon feed stream, i.e., cc of liquid feed per cc of catalyst per hour, is about 0.1 to about 15, and the reaction pressure is within the range of 200 psig to about 1500 psig in the isomerization zone. The gas hourly space velocity of the hydrogen stream is generally about 10–2,000 (preferably about 50–200) cc $H_2$ per cc catalyst per hour (so as to provide the above-recited $H_2$:alkane ratio). The isomerization product, i.e., the effluent exiting the isomerization reaction zone, can be subjected to any suitable separation (preferably fractional distillation) to separate the desired formed product isomers (e.g., isopentanes) from unconverted feed hydrocarbon (e.g., n-pentane) and from other hydrocarbons which may be present in the product. The desired product isomer is thus recovered from the effluent.

In the process of this invention, one or more sulfur compounds are present as impurities in the isomerization feed stream. The at least one sulfur compound may be contained in the hydrogen feed stream but generally is contained in the saturated hydrocarbon feed stream. Since these two feed streams are combined to form the isomerization feed stream (which is contacted with the catalyst), the exact source of the S compound(s) is not critical. Non-limiting examples of sulfur compounds which can be present in the feed stream include hydrogen sulfide, carbonyl sulfide (COS), carbon disulfide, methyl mercaptan, ethyl mercaptan, n-propyl mercaptan, isopropyl mercaptan, n-butyl mercaptan, isobutyl mercaptan, dimethyl sulfide, diethyl sulfide, methyl ethyl sulfide, methyl n-propyl sulfide, ethyl n-propyl sulfide, ethyl isopropyl sulfide, dimethyl disulfide, diethyl disulfide, methyl ethyl disulfide, methyl n-propyl disulfide, ethyl n-propyl disulfide, di(n-propyl) disulfide, methyl isopropyl disulfide, ethyl isopropyl disulfide, diisopropyl disulfide, methyl n-butyl disulfide, ethyl n-butyl disulfide, propyl n-butyl disulfide, di(n-butyl) disulfide, methyl isobutyl disulfide, ethyl isobutyl disulfide, propyl isobutyl disulfide, diisobutyl disulfide, dimethyl trisulfide, dimethyl tetrasulfide, and the like, and mixtures of two or more than two of the above sulfur compounds. Generally, the total sulfur content in the isomerization feed (on an elemental basis, based on the weight of said at least one feed hydrocarbon) attributed to all sulfur compounds present in the isomerization feed is about 1–2,000 ppm S (i.e., 1–2,000 parts by weight of sulfur per million parts by weight of said at least one saturated feed hydrocarbon). In most cases, the sulfur content is about 10–200 ppm S. In addition to sulfur compounds, other impurities may also be present in the isomerization feed, such as water, carbon dioxide, carbon monoxide, and aromatics (such as benzene). The amounts of these additional impurities must be small enough that they do not have detrimental effects on the process of this invention.

The amount of water in the isomerization feed is either essentially nil or is not to exceed about 60 ppm $H_2$(60 parts by weight of $H_2O$ per million parts by weight of the at least one saturated feed hydrocarbon), and preferably should not exceed about 45 ppm $H_2O$. Thus, the hydrocarbon feed should be dried (employing an effective desiccant, such as silica gel, $CaCl_2$, alumina, molecular sieves and the like), so as to reduce the water content of the feed to about 60 ppm $H_2O$ or less, preferably to about 45 ppm $H_2O$ or less, more preferably to about 0–30 ppm $H_2O$. It is, of course, also necessary to use sufficiently dry hydrogen gas (which is mixed with the hydrocarbon feed) and to employ, if necessary, a desiccant (such as described above) to dry the hydrogen stream, so as to ensure that the isomerization feed mixture of feed hydrocarbon and hydrogen does not contain more than about 60 ppm $H_2O$ (based on the weight of the feed hydrocarbon portion of the isomerization feed).

The sulfur compounds (generally in conjunction with water) cause the isomerization catalyst to lose its activity, thus resulting in the production of less of the desired isomer product(s). The presence of excessive amounts of water impurities (i.e., in excess of about 60 ppm $H_2O$, as defined above) will exacerbate the activity loss. The more detrimental sulfur compounds are those having higher boiling points (in particular alkyl mercaptans with 4 or more than 4 carbon atoms per molecule, dialkyl sulfides with a total of 4 or more than 4 carbon atoms per molecule, dialkyl disulfides with a total of 3 or more than 3 carbon atoms per molecule, and dialkyl polysulfides with 3 or more than 3 carbon atoms per molecule). The catalyst deactivating effect of these sulfur compounds is counteracted in the process of this invention by adding at least one volatile chlorine compound (also referred to as "chloride additive") to the feed mixture containing said at least one feed hydrocarbon and hydrogen in an effective amount (which will depend on the types and amounts of the sulfur compounds present). It is also feasible to inject the chloride additive into the hydrocarbon feed stream or into the hydrogen gas feed stream. Since both of these feed streams are mixed (to form the isomerization feed mixture) before their contact with the catalyst, the end result will be essentially the same as injecting the chloride additive into the combined isomerization feed mixture (containing at least one saturated feed hydrocarbon and $H_2$).

HCl can be used as the chloride additive, but organic chlorides are presently preferred. Effective organic chlorides include (but are not limited to) chloroalkanes, chlorocycloalkanes and chloroalkenes, generally containing up to 6 carbon atoms and up to 8 chlorine atoms per molecule, preferably monochloromethane, dichloromethane, trichloromethane (chloroform), tetrachloromethane (carbon tetrachloride; presently more preferred), monochloroethane, dichloroethanes, trichloroethanes, tetrachloroethanes, pentachloroethane, hexachloroethane, monochloropropanes, dichloropropanes, trichloropropanes, tetrachloropropanes, pentachloropropanes, hexachloropropanes, heptachloropropanes, octachloropropane, monochlorobutane, dichlorobutanes, trichlorobutanes, tetrachlorobutanes, monochloropentane, dichloropentanes, trichloropentanes, tetrachloropentanes, monochlorocyclopentane, chlorohexanes, and dichlorocyclopentanes, trichlorocyclopentanes, monochlorocyclohexane, dichlorocyclohexanes, trichlorocyclohexanes, monochloroethylene, 1,1-dichloroethylene, 1,2-dichloroethylene, trichloroethylene, tetrachloroethylene (perchloroethylene, PEC; presently most preferred), chloropropylenes, chloro-n-butenes, chloroisobutenes, chloropentenes, mixtures comprising any of the above organic chloride compounds, and mixtures comprising HCl and any of the above organic chloride compounds.

In the process of this invention, the isomerization feed or, alternatively, the feed hydrocarbon stream is generally analyzed (at various time intervals, preferably by means of a gas chromatograph) so as to detect which sulfur compounds are present and in which amounts each sulfur compound is present in the feed. From calibration curves (presented later), the effective amount of the added chloride which is required to essentially eliminate the catalyst deactivating effect of all sulfur compounds is determined, so as to assure a satisfactory and substantially constant feed conversion (to product isomers). Generally, the effective amount of added chloride corresponds to about 0.01–1 ppb Cl (i.e., about 0.01–1 part by weight Cl per billion parts by weight of said at least one saturated feed hydrocarbon) per 1 ppm S (i.e., one part by weight sulfur per million parts by weight of said saturated feed hydrocarbon; see FIG. 1 ). The chloride additive is generally injected either into the hydrocarbon feed stream or into the hydrogen gas stream or into the mixture of hydrocarbon feed and hydrogen gas which is passed into the isomerization reactor. It is believed (even though we do not wish to be bound by this theory) that the chloride additive reacts with the sulfur impurities (which are adsorbed on the catalyst surface) at the reaction conditions of the isomerization process so as to form volatile gases (such as $H_2S$ and HCl) which are swept away from the catalyst. $H_2S$ and HCl can be removed from the isomerization product (if desired) by any effective means of adsorbing or absorbing $H_2S$ and HCl, such as soda-lime, amines and the like.

The following examples are presented to further illustrate the invention and are not to be considered as unduly limiting the scope of the invention.

EXAMPLE I

In this example, lab-scale tests are described to illustrate the process of this invention.

A stainless-steel reactor (having an inner diameter of about 0.75 inch and a height of about 31 inches) was filled with a layer ( 14 inches high) of Alundum® (inert alumina particles having a surface area of 1 $m^2/g$ or less), a layer (10 inches high) of I-7 Pt/zeolite isomerization catalyst (marketed by UOP, Des Plaines, Ill.; containing about 0.25 weight-% Pt, about 35 weight-% Si, about 9 weight-% Al, about 0.3 weight-% Mg, about 0.15 weight-% Na, and the remainder being essentially chemically bound O and H; halogen content: essentially nil; surface area: 452 $m_2/g$) and a bottom layer (12 inches high) of Alundum®. The reactor contents were heated to about 500° F., and a liquid alkane-containing feed (containing about 91 weight-%-n-pentane) was introduced into the reactor at a liquid hourly space velocity of about 40 cc/hour (liquid hourly space velocity: about 2 cc/cc/hour), together with hydrogen gas at a flow rate of about 66 cc/minute, so as to provide a molar ratio of $H_2$ to n-pentane of about 0.5:1. This alkane-containing feed also contained about 4 weight-% isopentanes, small amounts of $C_6$ alkanes, 27 ppm water, and various sulfur impurities (primarily methyl ethyl sulfide, and carbon disulfide) equivalent to a total sulfur content of 6 ppm S (on an elemental basis). The reaction pressure was about 400 psig. The obtained isomerization product (containing isopentanes and unconverted n-pentane) was analyzed by means of a gas chromatograph. The molar ratio of formed isopentanes to all pentanes (i.e., n-pentane and isopentanes) in the product, also referred to as product ratio (PR), was determined and was considered a reliable measure of the catalyst activity.

In preliminary lab tests, a gradual decrease of PR values in n-pentane isomerization reactions using an I-7 catalyst was observed. It was concluded that this catalyst deactivation (indicated by decreasing PR values) was caused by the accumulation of sulfur impurities (contained in the n-pentane feed) on the catalyst. It was also observed in these preliminary tests that the presence of an organic chloride ($CCl_4$) in the feed was beneficial in alleviating the above-described catalyst deactivation.

In order to confirm these preliminary observations and to determine how much of an organic chloride additive is needed to counteract the catalyst-deactivating effect of sulfur compounds which are present in a n-pentane feed, various amounts of several sulfur compounds and of an organic chloride (tetrachloroethylene; also called perchloroethylene, PCE; obtained from PPG Corporation Chemical Group, Pittsburgh, Pa.) were added to the isomerization feed (described above) which was then isomerized at the above-described isomerization conditions (reaction temperature: 500° F.; reaction pressure: 400 psig; $H_2$ to n-pentane molar ratio: 0.5:1;I-7 catalyst). In these particular lab tests, PCE was injected into the hydrogen gas stream (however, it is to be understood that PCE, or any other chloride additive, may also be injected into saturated hydrocarbon feed stream or into a combined hydrocarbon/$H_2$ isomerization stream). Test results are summarized in Table I.

TABLE I

| Run | Hours on Stream | Added Sulfur Compound | ppm S Added[1] | ppb Cl Added[2] | PR (%)[3] |
|---|---|---|---|---|---|
| 1 | 0 | MES[4] | 48 | 0 | 60.7 |
|   | 24 | " | " | " | 59.8 |
|   | 70 | " | " | " | 59.7 |
| 2 | 0 | MES[4] | 48 | 3 | 60.3 |
|   | 53 | " | " | " | 61.2 |
|   | 125 | " | " | " | 61.2 |
|   | 269 | " | " | " | 61.6 |
| 3 | 0 | MES[4] | 206 | 14 | 61.5 |
|   | 24 | " | " | " | 61.7 |
|   | 70 | " | " | " | 61.9 |
| 4 | 0 | ESH[5] | 226 | 14 | 65.0 |
|   | 14 | " | " | " | 65.2 |
| 5 | 0 | ESH[5] | 226 | 76 | 64.0 |
|   | 40 | " | " | " | 66.5 |
| 6 | 0 | DBDS[6] | 32 | 3 | 62.7 |
|   | 18 | " | " | " | 60.4 |
| 7 | 0 | DBDS[6] | 32 | 18 | 60.9 |
|   | 25 | " | " | " | 59.4 |
| 8 | 0 | DBDS[6] | 32 | 36 | 62.3 |
|   | 20 | " | " | " | 62.5 |

[1]parts by weight of added S (in the form of a particular organic sulfur compound) per million parts by weight of feed
[2]parts by weight of added Cl (in the form of perchloroethylene) per billion parts by weight of feed
[3]product ratio; weight ratio of isopentanes to all pentanes (i.e., isopentanes and unconverted n-pentane) in product
[4]methyl ethyl sulfide
[5]ethyl mercaptan
[6]dibutyl disulfide Test data in Table I confirm that sulfur compounds indeed cause isomerization catalyst deactivation and that this deactivation can be completely eliminated when a sufficient amount of an organic chloride compound is added to the isomerization feed. These test data also show that some sulfur compounds caused more extensive catalyst deactivation than others (compare the effect of 32 ppm DBDS with the effect of 48 ppm MES). In the case of DBDS, even the addition of up to 18 ppm Cl was not sufficient to eliminate the catalyst deactivation effect; it required 36 ppm added Cl to eliminate DBDS-caused catalyst deactivation.

EXAMPLE II

This example illustrates an empirical correlation between (a) the amount of added organic chloride (on an elemental Cl basis) required to counteract catalyst deactivation caused by particular sulfur compounds and (b) a specific parameter of each particular sulfur compound.

In a series of tests (substantially according to the test procedure described in Example I) it was confirmed that smaller amounts of the chloride additive were needed to eliminate isomerization catalyst deactivation when relatively low boiling sulfur compounds (such as methyl mercaptan, ethyl mercaptan, dimethyl sulfide) were present in the feed, and larger amounts of added chloride were needed when higher boiling sulfur compounds (such as diethyl disulfide, dipropyl disulfide, dibutyl disulfide) were present in the feed. The water content in the feed was about 30 ppm $H_2O$ (based on the weight of feed hydrocarbon) in all tests.

A quantitative correlation was established between (a) the minimum amount of added chloride (ppb Cl, as defined above) required to eliminate the catalyst deactivating effect of 1 ppm S (as defined above) of various sulfur compounds (ppb Cl/ppm S) and (b) the ratio of the normal boiling point $T_b$, (°F., measured at 1 atm) of various sulfur compounds to the n-pentane isomerization reaction temperature $T_i$ (°F.). FIG. 1 illustrates this above-described correlation for the following sulfur compounds: methyl mercaptan (MSH), ethyl mercaptan (ESH), dimethyl sulfide (DMS), methyl ethyl sulfide (MES), isobutyl mercaptan (IBSH), dimethyl disulfide (DMDS), diethyl disulfide (DEDS), di(n-propyl) disulfide (also referred to dipropyl disulfide; DPDS) and di(n-butyl) disulfide (also referred to as dibutyl disulfide; DBDS). The water content in the feed is to be about 30 ppm $H_2O$ or less.

When a n-pentane feed contains various amounts of more than one sulfur compound, the total amount of added chloride (on an elemental basis) is calculated as follows: First, the amount of each sulfur compound in the feed is determined (e.g., by means of a chromatograph). Then the minimum amount of added chloride (ppb Cl, as defined above) required to eliminate the catalyst deactivating effect at the isomerization temperature caused by 1 ppm S (as defined above) attributed to each individual sulfur compound is determined using the graph in FIG. 1. Finally, the sum of added Cl amounts required for each sulfur compound is calculated, thus obtaining the total minimum amount of Cl required to counteract the catalyst deactivating effects of all sulfur compounds present in the feed. For instance, if n-pentane feed contains 31 ppm S in the form of methyl ethyl sulfide (MES) and 32 ppm S in the form of dibutyl disulfide (DBDS), the total minimum amount of added chloride (ppb Cl, as defined above) to eliminate the catalyst deactivation caused by both sulfur compounds is calculated as follows:

$$31 \times (ppm\ Cl/ppm\ S\ for\ MES) + 32 \times (ppb\ Cl/ppm\ S\ for\ DBDS) = 31 \times 0.042 + 32 \times 1.06 = 35\ ppbCl.$$

This calculated result was experimentally confirmed by adding about 41 ppb Cl (i.e., a 10% excess over the calculated minimum amount of 35 ppm Cl) in the form of perchloroethylene to a n-pentane/$H_2$ isomerization feed which also contained 27 ppm $H_2O$, 31 ppm MES and 32 ppm DBDS as impurities. The n-pentane feed (containing the above impurities) was passed, together with hydrogen gas (into which the chloride additive had been injected), into an isomerization reactor which contained an I-7 catalyst and was heated to a reaction temperature of 500° F., essentially in accordance with the procedure outlined in Example I. Test data for this test run are summarized in Table II.

TABLE II

| Hours on Stream | PR[1] |
|---|---|
| 10 | 61.5 |
| 35 | 62.8 |
| 60 | 63.6 |
| 80 | 63.8 |
| 100 | 63.5 |
| 120 | 63.4 |
| 145 | 63.4 |

[1]see footnote 3 in Table I

Test data in Table II clearly show that during the entire isomerization test, no catalyst activation had occurred, i.e., the potential deactivation of the I-7 catalyst by 31 ppm MES and 32 ppm DBDS was completely eliminated by the addition to the isomerization feed of an amount of perchloroethylene equivalent to 41 ppb Cl.

EXAMPLE III

This example illustrates that the chloride addition to an alkane isomerization feed which contains sulfur compounds (as described in Examples I and II) is effective only when the water content in the isomerization feed is sufficiently low (not more than about 60 ppm $H_2O$, as defined above).

In a series of isomerization tests (essentially in accordance with the procedure described in Example I, employing an n-pentane feed and an I-7 catalyst at a reaction temperature of 500° F.) various amounts of water were present in the feed: 25 ppm $H_2O$, 45 ppm $H_2O$, 65 ppm $H_2O$, and, 85 ppm $H_2O$, respectively. The feed also contained 32 ppm S in the form of dibutyl disulfide (DBDS). The addition of chloride (in the form of perchloroethylene) to the isomerization feed which was required to substantially eliminate catalyst deactivation caused by 32 ppm S in the form of DBDS was determined using the graph of FIG. 1. This calculated amount was about 1.1 ppb Cl per 1.0 ppm S. When the water content in the feed was about 25 ppm $H_2O$, indeed no decrease in the PR value was observed (thus no catalyst deactivation occurred) when 1.1 ppb Cl (in the form of PEC) per ppm S was added to the feed. When the water content in the feed was about 45 ppm, a slight catalyst deactivation already occurred when about 1.1 ppb Cl per ppm S was added (as indicated by a very small decrease in PR value of about 0.01 per hour). However, when the feed contained 65 ppm $H_2O$, not even the addition of 2.3 ppb Cl per ppm S (i.e., twice the calculated amount) was adequate to prevent catalyst deactivation (observed decrease in PR value: 0.06 per hour); and when the feed contained 85 ppm $H_2O$, not even the addition of 13.5 ppb Cl per ppm S (i.e., 12 times the calculated amount) was adequate to prevent rapid catalyst deactivation (observed decrease in PR value: about 0.15 per hour).

Based on the above-described test results it is concluded that in the process of this invention, the feed should not contain more than about 60 ppm $H_2O$ (based on the feed hydrocarbon portion of the isomerization feed). Preferably, the feed should not contain more than about 45 ppm water, and more preferably not more than about 30 ppm $H_2O$. Thus, the conelation shown in FIG. 1 is most successfully applied when the water content in the feed is in the range of about 0–30 ppm water. When the water content is in excess of 30 ppm water but does not exceed about 45 ppm $H_2O$, the amount of ppb Cl/ppm S required for eliminating the catalyst deactivation by particular sulfur compounds should be increased by a factor, which is estimated to range from about 1.1 (for a water content of about 35 ppm $H_2O$) to about 1.5 (for a water content of about 45 ppm $H_2O$). In the range of about 46–60 ppm $H_2O$, this correction factor probably ranges from about 1.6 to about 5. When the amount of water present in the feed is greater than about 60 ppm $H_2O$, the elimination (or substantial alleviation) of the catalyst deactivating effect caused by sulfur compounds can no longer be accomplished by chloride addition to the feed in accordance with the process of this invention.

Reasonable variations, modifications and adaptation for various conditions and reactants can be made within the scope of the disclosure and the appended claims without departing from the scope of this invention.

That which is claimed:

1. In an isomerization process for converting at least one saturated feed hydrocarbon selected from the group consisting of alkanes containing 4–10 carbon atoms per molecule and cycloalkanes containing 5–10 carbon atoms per molecule to at least one saturated product hydrocarbon isomer, wherein a feed stream which comprises (i) said at least one saturated feed hydrocarbon, (ii) hydrogen gas, (iii) about 0–60 parts by weight of water per million parts by weight of said at least one feed hydrocarbon, and (iv) at least one sulfur compound being present as an impurity is contacted in a reaction zone at effective isomerization conditions with a catalyst which consists essentially of platinum and at least one zeolite, and wherein deactivation of said catalyst is caused by said at least one sulfur compound in said reaction zone, the improvement which comprises eliminating the deactivation of said catalyst caused by said at least one sulfur compound by having at least one added chlorine compound selected from the group consisting of hydrogen chloride and organic chlorides present in said reaction zone.

2. A process in accordance with claim 1, wherein said at least one sulfur compound is present in said feed stream at a concentration corresponding to about 1–2,000 parts by weight of sulfur on an elemental basis per million parts by weight of said at least one saturated feed hydrocarbon.

3. A method in accordance with claim 2, wherein said concentration of at least one sulfur compound in said feed corresponds to about 10–200 parts by weight of sulfur per million parts by weight of said at least one saturated feed hydrocarbon.

4. A method in accordance with claim 2, wherein said at least one sulfur compound is selected from the group consisting of hydrogen sulfide, carbon disulfide, carbonyl sulfide, mercaptans, organic sulfides, organic disulfides and organic polysulfides.

5. A process in accordance with claim 4, wherein said at least one sulfur compound is selected from the group consisting of carbonyl sulfide, carbon disulfide, methyl mercaptan, ethyl mercaptan, n-propyl mercaptan, isopropyl mercaptan, n-butyl mercaptan, isobutyl mercaptan, dimethyl sulfide, diethyl sulfide, methyl ethyl sulfide, methyl n-propyl sulfide, ethyl n-propyl sulfide, ethyl isopropyl sulfide, dimethyl disulfide, diethyl disulfide, methyl ethyl disulfide, methyl n-propyl disulfide, ethyl n-propyl disulfide, di(n-propyl) disulfide, methyl isopropyl disulfide, ethyl isopropyl disulfide, diisopropyl disulfide, methyl n-butyl disulfide, ethyl n-butyl disulfide, propyl n-butyl disulfide, di(n-butyl) disulfide, methyl isobutyl disulfide, ethyl isobutyl disulfide, propyl isobutyl disulfide, diisobutyl disulfide, dimethyl trisulfide, dimethyl tetrasulfide, and mixtures thereof.

6. A process in accordance with claim 2, wherein the water content in said feed stream is about 0–45 parts by weight $H_2O$ per million parts by weight of said at least one saturated hydrocarbon.

7. A process in accordance with claim 6, wherein the water content in said feed stream is about 0–30 parts by weight $H_2O$ per million parts by weight of said at least one saturated hydrocarbon.

8. A process in accordance with claim 7, wherein said at least one saturated hydrocarbon is n-pentane.

9. A process in accordance with claim 1, wherein at least one added chlorine compound is at least one organic chloride selected from the group consisting of monochloromethane, dichloromethane, trichloromethane, carbon tetrachloride, monochloroethane, dichloroethanes, trichloroethanes, tetrachloroethanes, pentachloroethane, hexachloroethane, monochloropropanes, dichloropropanes, trichloropropanes, tetrachloropropanes, pentachloropropanes, hexachloropropanes, heptachloropropanes, octachloropropane, monochlorobutane, dichlorobutanes, trichlorobutanes, tetrachlorobutanes, monochloropentane, dichloropentanes, trichloropentanes, tetrachloropentanes, chlorohexanes, monochlorocyclopentane, dichlorocyclopentanes, trichlorocyclopentanes, monochlorocyclohexane, dichlorocyclohexanes, trichlorocyclohexanes, monochloroethylene, 1,1-dichloroethylene, 1,2-dichloroethylene, trichloroethylene, tetrachloroethylene, chloropropylenes, chloro-n-butenes, chloroisobutenes, chloropentenes, and mixtures comprising any of the above-listed organic chlorides.

10. A process in accordance with claim 9, wherein said at least one organic chloride is selected from the group consisting of carbon tetrachloride and tetrachloroethylene.

11. A process in accordance with claim 1, wherein the amount of said at least one added chlorine compound corresponds to about 0.01–1 part by weight of added Cl per billion parts by weight of said at least one saturated feed hydrocarbon for each part by weight S, attributed to said at least one sulfur compound, per million parts by weight of said at least one saturated feed hydrocarbon.

12. A process in accordance with claim 1, wherein said at least one saturated feed hydrocarbon is selected from the group consisting of normal alkanes containing 4–10 carbon atoms per molecule and cycloalkanes containing 5–10 carbon atoms per molecule.

13. A process in accordance with claim 12, wherein said at least one saturated feed hydrocarbon is n-pentane.

14. A process in accordance with claim 1, wherein the zeolite contained in said isomerization catalyst is mordenite.

15. A process in accordance with claim 14, wherein said isomerization catalyst contains about 0.05–2.0 weight-% Pt.

16. A process in accordance with claim 1, wherein said effective isomerization conditions comprise a reaction temperature of about 200°–600° F. and a molar ratio of hydrogen gas to said at least one saturated feed hydrocarbon in the range of about 0.01:1 to about 10:1.

17. A process in accordance with claim 16, wherein said saturated feed hydrocarbon is n-pentane, said reaction temperature is about 450°–550° F., the molar ratio of hydrogen gas to n-pentane is about 0.1 to about 1:1, and the reaction pressure is about 200–1500 psig.

18. A process in accordance with claim 1, wherein said at least one product hydrocarbon isomer is recovered from the effluent exiting said reaction zone.

19. A process in accordance with claim 1, wherein said at least one sulfur compound is selected from the group consisting of methyl mercaptan, ethyl mercaptan, dimethyl sulfide, methyl ethyl sulfide, isobutyl mercaptan, dimethyl disulfide, diethyl disulfide, di(n-propyl) disulfide and di(n-butyl) disulfide;

prior to the addition of said at least one chlorine compound to said reaction zone, the amount of each sulfur compound being selected from said group in said feed stream is determined by means of a chromatograph;

the amount of said at least one chlorine compound which is to be added to said reaction zone so as to eliminate the deactivation of said catalyst caused by each sulfur compound selected from said group is determined employing the correlation presented in FIG. 1; and the total amount of said at least one chlorine compound which is to be added to said reaction zone so as to eliminate the deactivation of said catalyst caused by all sulfur compounds selected from said group is calculated.

20. In an isomerization process for converting at least one saturated feed hydrocarbon selected from the group consisting of alkanes containing 4–10 carbon atoms per molecule and cycloalkanes containing 5–10 carbon atoms per molecule to at least one saturated product hydrocarbon isomer, wherein a feed stream which comprises (i) said at least one saturated feed hydrocarbon, (ii) hydrogen gas, (iii) about 0–60 parts by weight of water per million parts by weight of said at least one feed hydrocarbon, and (iv) at least one sulfur compound being present as an impurity is contacted in a reaction zone at effective isomerization conditions with a catalyst which consists essentially of platinum and at least one zeolite, and wherein deactivation of said catalyst is caused by said at least one sulfur compound in said reaction zone, the improvement which comprises counteracting said deactivation of said catalyst caused by said at least one sulfur compound by having at least one added chlorine compound selected from the group consisting of hydrogen chloride and organic chlorides present in said reaction zone in an amount equivalent to a ratio of ($\alpha$) about 0.01–1 part by weight of added chlorine per billion parts by weight of said at least one saturated feed hydrocarbon to ($\beta$) one part by weight of sulfur, attributed to said at least one sulfur compound, per million parts by weight of said saturated feed hydrocarbon.

21. A process in accordance with claim 20, wherein said at least one sulfur compound is present in said feed stream at a concentration corresponding to about 1–2,000 parts by weight of sulfur on an elemental basis per million parts by weight of said at least one saturated feed hydrocarbon.

22. A method in accordance with claim 21, wherein said concentration of at least one sulfur compound in said feed corresponds to about 10–200 parts by weight of sulfur per million parts by weight of said at least one saturated feed hydrocarbon.

23. A method in accordance with claim 21, wherein said at least one sulfur compound is selected from the group consisting of hydrogen sulfide, carbon disulfide, carbonyl sulfide, mercaptans, organic sulfides, organic disulfides and organic polysulfides.

24. A process in accordance with claim 23, wherein said at least one sulfur compound is selected from the group consisting of carbonyl sulfide, carbon disulfide, methyl mercaptan, ethyl mercaptan, n-propyl mercaptan, isopropyl mercaptan, n-butyl mercaptan, isobutyl mercaptan, dimethyl sulfide, diethyl sulfide, methyl ethyl sulfide, methyl n-propyl sulfide, ethyl n-propyl sulfide, ethyl isopropyl sulfide, dimethyl disulfide, diethyl disulfide, methyl ethyl disulfide, methyl n-propyl disulfide, ethyl n-propyl disulfide, di(n-propyl) disulfide, methyl isopropyl disulfide, ethyl isopropyl disulfide, diisopropyl disulfide, methyl n-butyl disulfide, ethyl n-butyl disulfide, propyl n-butyl disulfide, di(n-butyl) disulfide, methyl isobutyl disulfide, ethyl isobutyl disulfide, propyl isobutyl disulfide, diisobutyl disulfide, dimethyl trisulfide, dimethyl tetrasulfide, and mixtures thereof.

25. A process in accordance with claim 21, wherein the water content in said feed stream is about 0–45 parts by weight $H_2O$ per million parts by weight of said at least one saturated feed hydrocarbon.

26. A process in accordance with claim 25, wherein the water content in said feed stream is about 0–30 parts by weight $H_2O$ per million parts by weight of said at least one saturated feed hydrocarbon.

27. A process in accordance with claim 26, wherein said at least one saturated feed hydrocarbon is n-pentane.

28. A process in accordance with claim 20, wherein at least one added chlorine compound is at least one organic chloride selected from the group consisting of monochloromethane, dichloromethane, trichloromethane, carbon tetrachloride, monochloroethane, dichloroethanes, trichloroethanes, tetrachloroethanes, pentachloroethane, hexachloroethane, monochloropropanes, dichloropropanes, trichloropropanes, tetrachloropropanes, pentachloropropanes, hexachloropropanes, heptachloropropanes, octachloropropane, monochlorobutane, dichlorobutanes, trichlorobutanes, tetrachlorobutanes, monochloropentane, dichloropentanes, trichloropentanes, tetrachloropentanes, chlorohexanes, monochlorocyclopentane, dichlorocyclopentanes, trichlorocyclopentanes, monochlorocyclohexane, dichlorocyclohexanes, trichlorocyclohexanes, monochloroethylene, 1,1-dichloroethylene, 1,2-dichloroethylene, trichloroethylene, tetrachloroethylene, chloropropylenes, chloro-n-butenes, chloroisobutenes, chloropentenes, and mixtures comprising any of the above-listed organic chlorides.

29. A process in accordance with claim 28, wherein said at least one organic chloride is selected from the group consisting of carbon tetrachloride and tetrachloroethylene.

30. A process in accordance with claim 20, wherein said at least one saturated feed hydrocarbon is selected from the group consisting of normal alkanes containing 4–10 carbon atoms per molecule and cycloalkanes containing 5–10 carbon atoms per molecule.

31. A process in accordance with claim 30, wherein said at least one saturated feed hydrocarbon is n-pentane.

32. A process in accordance with claim 20, wherein the zeolite contained in said isomerization catalyst is mordenite.

33. A process in accordance with claim 32, wherein said isomerization catalyst contains about 0.05–2.0 weight-% Pt.

34. A process in accordance with claim 20, wherein said effective isomerization conditions comprise a reaction temperature of about 200°–600° F. and a and a molar ratio of hydrogen gas to said at least one saturated feed hydrocarbon in the range of about 0.01:1 to about 10:1.

35. A process in accordance with claim 34, wherein said saturated feed hydrocarbon is n-pentane, said reaction temperature is about 450°–550° F., the molar ratio of hydrogen gas to n-pentane is about 0.1 to about 1:1, and the reaction pressure is about 200–1500 psig.

36. A process in accordance with claim 20, wherein said at least one product hydrocarbon isomer is recovered from the effluent exiting said reaction zone.

37. A process in accordance with claim 20, wherein said counteracting results in alleviating said deactivation of said catalyst.

* * * * *

UNITED STATES PATENT AND TRADEMARK OFFICE
CERTIFICATE OF CORRECTION

PATENT NO.   : 5,557,029

DATED        : September 17, 1996

INVENTOR(S)  : Fan-Nan Lin, Nak J. Sung, Stephen L. Ege, and Thomas A. Lessard

It is certified that error appears in the above-identified patent and that said Letters Patent is hereby corrected as shown below:

Column 10, claim 6, line 6, insert --- feed --- between "saturated" and "hydrocarbon".

Column 10, claim 7, line 9, insert --- feed --- between "saturated" and "hydrocarbon".

Column 10, claim 8, line 11, insert --- feed --- between "saturated" and "hydrocarbon".

Column 11, claim 20, line 22, delete "pans" and insert --- parts --- therefor.

Signed and Sealed this

Seventeenth Day of December, 1996

Attest:

BRUCE LEHMAN

*Attesting Officer*          *Commissioner of Patents and Trademarks*